US007033612B2

(12) United States Patent
Kang et al.

(10) Patent No.: US 7,033,612 B2
(45) Date of Patent: Apr. 25, 2006

(54) COMPOSITION AND METHOD FOR TREATING AGE-RELATED DISORDERS

(76) Inventors: David S. Kang, 16 Forest Gate Cir., Oakbrook, IL (US) 60523; Chunghee Kimberly Kang, 16 Forest Gate Cir., Oakbrook, IL (US) 60523

(*) Notice: Subject to any disclaimer, the term of this patent is extended or adjusted under 35 U.S.C. 154(b) by 459 days.

(21) Appl. No.: 10/336,150

(22) Filed: Jan. 3, 2003

(65) Prior Publication Data
US 2004/0131644 A1 Jul. 8, 2004

(51) Int. Cl.
*A61K 35/54* (2006.01)
(52) U.S. Cl. .................. 424/582; 424/283.1; 424/450; 424/465
(58) Field of Classification Search ............... 424/582, 424/283.1, 450, 465, 581
See application file for complete search history.

(56) References Cited

U.S. PATENT DOCUMENTS

| 5,484,611 | A |   | 1/1996  | Noble |
|-----------|---|---|---------|-------|
| 5,780,615 | A | * | 7/1998  | Bucala et al. ............. 536/29.1 |
| 5,801,200 | A | * | 9/1998  | Bucala et al. ............. 514/634 |
| 6,300,377 | B1 |  | 10/2001 | Chopra |
| 6,500,843 | B1 | * | 12/2002 | Steiner et al. ............. 514/317 |
| 6,514,973 | B1 | * | 2/2003  | Buchholz et al. .......... 514/249 |
| 2004/0234544 | A1 | * | 11/2004 | Jager et al. ............. 424/195.15 |
| 2004/0234587 | A1 | * | 11/2004 | Sampalis ................ 424/450 |

FOREIGN PATENT DOCUMENTS

EP 0 437 334 B1 8/1995

OTHER PUBLICATIONS

R. Franson et al, *Solubilization and Characterization of a Neutral- Active, Calcium-Dependant, Phosholipase $A_2$ from Rabbit Heart and Isolated Chick Embryo Myocytes*, J. Mol. Cell Cardiol. 15: 189-196 (1983).
M. Mehlman et al, *Studies on the Distribution of Free Carnitine and the Occurrence and Nature of Bound Carnitine*, Arch. Biochem. Biophys. 98: 146-153 (1962).
F. Granata et al, *Phosphocholine and phosphoethanolamine During Chick Embryo Myogenesis: a $^{31}$P-NMR Study*, Biochem. Biophys. Acta 1483: 334-342 (2000).
L. Allen et al, *Partial Phenotypic Suppression of a Peroxisome-deficient Animal Cell Mutant Treated with Aminoglycoside G418*, J. Biol. Chem. 267: 13191-13199 (1992).
G. Arthur et al, *The Distribution and Acyl Composition of Plasmalogens in Guinea Pig Heart*, Lipids 20:693-698 (1985).
J. Brook et al, *Dietary Soya Lecithin Decreases Plasma Triglyceride Levels and Inhibits Collagen- and ADP-Induced Platelet Aggregation*, Biochem. Med. Metab. Biol. 35:31-39 (1986).

I. Carrie et al, *Phospholipid Supplementation Reverses Behavioral and Biochemical Alterations Induced by N-3 Polyunsaturated Fatty Acid Deficiency in Mice*, J. Lipid Res. 41:473-480 (2000).
X. Chen et al, *Potassium Flux through Gramicidin Ion Channels is Augmented in Vesicles Comprised of Plasmenylcholine: Correlations between Gramicidin Conformation and Function in Chemically Distinct Host Bilayer Matrices*, Biochemistry 34:7356-7364 (1995).
K. Chepenik et al, *On the Presence of Plasmologens in Developing Rat Embryos*, Int. J. Biochem. 11:605-607 (1980).
I. Delton-Vandenbroucke et al, *Dual Regulation of Glutathione Peroxidase by Docosahexaenoic Acid in Endothelial Cells Depending on Concentration and Vascular Bed Origin*, Free Radical Biol. Med. 30:895-904 (2001).
A. Diagne et al, *Studies of Ether Phospholipids. II Comparative composition of various tissues from human, rat and guinea pig*, Biochim. Biophys Acta 793:221-231 (1984).
J. Duhm et al, *Accelerated Maximal Velcoity of the Red Blood Cell $Na^+/K^+$ Pump in Hyperlipidemia is Related to Increase in 1-palmitoyl,2-arachidonoyl-plasmalogen Phosphatidylethanolamine*, Biochim. Biophys. Acta 1149: 185-188 (1993).
B. Engelmann et al, *Plasmalogen Phospholipids as Potential Protectors against Lipid Peroxidation of Low Density Lipoproteins*, Biochem. Biophys. Res. Commun. 204:1235-1242 (1994).
H. Goldfine et al, *Phase Behavior of Ether Lipids from Clostridium Butyricum*, Biochemistry 20:2908-2916 (1981).
H. Goldfine et al, *Lipid Shape as a Determinant of Lipid Composition in Clostridium Butyricum: The Effects of Incorporation of Various Fatty Acids on the Ratios of the Major Ether Lipids*, Biochim. Biophys. Acta 904:283-289 (1987).

(Continued)

Primary Examiner—Herbert J. Lilling
(74) Attorney, Agent, or Firm—Brinks Hofer Gilson & Lione

(57) ABSTRACT

There is provided a composition for the prevention and treatment of age-related physical and mental disorders that includes phospholipids that have been extracted from chick embryos aged between about 6 days old and about 14 days old. Also provided is a method for extracting these phospholipids by incubating them for between about 6 days to about 14 days. The chick embryos are then prepared for chemical extraction, and the lipids are extracted from the chick embryos. Further provided is a method for preventing and treating age-related physical and mental disorders, in human subjects in need thereof, by administering a sufficient dosage of a composition including phospholipids extracted from chick embryos incubated for between about 6 days and about 14 days to a human subject.

31 Claims, No Drawings

OTHER PUBLICATIONS

M. Hack et al, *On the Plasmalogenation of Myocardial Choline Glycerophospholipid During Maturation of Various Vertebrates*, Comp. Biochem. Physiol. 89B:111-118 (1988).

S. Hazen et al, *Activation of a Membrane-Associated Phospholipase $A_2$ during Rabbit Myocardial Ischemia Which is Highly Selective for Plasmologen Substrate*, J. Biol. Chem. 266:5629-5633 (1991).

S. Hazen et al, *Purification and Characterization of Canine Myocardial Cytosolic Phospholipase $A_2$ A calcium-independent phospholipase with absolute f1-2 regiospecificity for diradyl glycerophospholipids*, J. Biol. Chem. 265:10622-10630 (1990).

N. Khaselev et al, *Susceptibility of Plasmenyl Glycerophosphoethanolamine Lipids Containing Arachidonate to Oxidative Degradation*, Free Radical Biol. Med. 26:275-284 (1999).

M. Lee et al, *Phospholipid Functional Groups Involved in Protein Kinase C Activation, Phorbol Ester Binding and Binding to Mixed Micelles*, J. Biol. Chem. 264:14797-14805 (1989).

M. Lee et al, *Supplementation of the Phosphatidyl-L-serine Requirement of Protein Kinase C with Nonactivating Phospholipids*, Biochemistry 31:5176-5182 (1992).

K. Lohner et al, *Phase Behavior of Ethanolamine Plasmalogen*, Chem. Phys. Lipids 34:163-170 (1984).

A. Maldjian et al, *The Transfer of Docosahexaenoic Acid from the Yolk to the Tissues of the Chick Embryo*, Biochim. Biophys. Acta 1258:81-89 (1995).

M. Martinez, *Docosahexaenoic Acid Therapy in Docosahexaenoic Acid-Deficient Patients with Disorders of Peroxisomal Biogenesis*, Lipids 31:S145-S152 (1996).

M. Martinez et al, *Therapeutic Effects of Docosahexaenoic Acid Ethyl Ester in Patient with Generalized Peroxisomal Disorders*, Am. J. Clin. Nutr. 71:376S-285S (2000).

N. Maulik et al, *Fatty Acid Profiles of Plasmalogen Choline and Ethanolamine Glycerophospholipids in Pig and Rat Hearts*, J. Pharmaceut. Biomed. Analysis 14: 49-56 (1995).

Y. Nakagawa et al, *Changes in the Composition of Fatty Chains of Diacyl, Alkylacyl and Alkenylacyl Ethanolamine and Choline Phosphoglycerides During the Development of Chick Heart Ventricular Cells*, Biochim. Biophys. Acta 712:667-676 (1982).

N. Nagan et al, *A Fibroblast Cell Line Defective in Alkyl-Dihydroxyacetone Phosphate Synthase: A Novel Defect in Plasmalogen Biosynthesis*, Proc. Natl. Acad. Sci. USA 94: 4475-4480 (1997).

D. Neel et al, *Changes in Phospholipids from Chick Fibroblasts during Embryo Development*, Biochem. Biophys. Res. Commun. 98:21-27 (1981).

A. Rizzo et al, *Phospholipid Distribution and Fatty Acid Composition in Different Brain Regions during Chick Embryo Development*, J. Neurochem. 64: 1728-1733 (1995).

P. Sindelar et al, *The Protective Role of Plasmologens in Iron-Induced Lipid Peroxidation*, Free Radical Biol. Med. 26: 318-324 (1999).

T. Sugiura et al, *Ether Lysophospholipid-induced Production of Platelet-Activating Factor in Human Polymorphonuclear Leukocytes*, Biochim. Biophys. Acta 1047:223-232 (1990).

P. Thome et al, *Clofibrate and Other Peroxisomal Proliferating Agents Relatively Specifically Inhibit Synthesis of Ethanolamine Phosphoglycerides in Cultured Human Fibroblasts*, Biochim. Biophys. Acta 1214:161-170 (1994).

L. Torello et al, *A Comparative-Evolutionary Study of Lipids in the Aging Brain of Mice*, Neurobiol. Aging 7:337-346 (1986).

Y. Uemura et al, *A Coenxyme A-independent Transacylase Is Linked to the Formation of Platelet-Activating Factor (PAF) by Generating the Lyso-PAF Intermediate in the Remodeling Pathway*, J. Biol. Chem. 266:8268-8272 (1991).

M. Venable et al, *Conversion of 1-O-[$^3$H]Alkyl-2-arachidonoyl-sn-glycero-3-phosphorylcholine to Lyso Platelet-activating Factor by the CoA-independent Transacylase in Membrane Fractions of Human Neutrophils*, J. Biol. Chem. 266:18691-18698 (1991).

J. Wojcicki et al, *Effects of "Essential" Phospholipids (EPL) on Experimental Ethanol-Induced Cardiomyopathy*, Arzneimit. Forsch. (Drug Rs.) 25:1420-1422 (1975).

R. Zoeller et al, *A Possible Role for Plasmalogens in Protecting Animal Cells against Photosensitized Killing*, J. Biol. Chem. 263:11590-11596 (1988).

\* cited by examiner

COMPOSITION AND METHOD FOR TREATING AGE-RELATED DISORDERS

FIELD OF THE INVENTION

The present invention is directed towards a composition and method for preventing and treating age-related disorders. More specifically, the present invention is directed towards a composition and method for treating age-related disorders using phospholipids extracted from chicken embryos aged from about 6 to about 14 days, prepared for oral or sublingual administration.

BACKGROUND OF THE INVENTION

The symptoms of aging affect the human body in both physical and mental ways. Aging of cells and tissues can affect a person's strength, stamina and agility. Aging of various cells and tissues can result in the diminished sensations of well-being, fatigue, delayed physical and mental recovery, diminished cognitive ability and insomnia. Further physical effects include skin aging, wrinkling, and discoloration, hair loss, decreased endurance and tolerance to physical and mental activities, and muscle fatigue. Neuro-endocrinological disorders, such as decreased sexual performance and maintenance of normal blood pressure and blood chemistry, are also closely associated with the aging of tissues. The physiological aging of the cellular and intracellular membranes of the human body is the cause of many of these age-related disorders.

The cellular and intracellular membranes of the human body are primarily comprised of lipids. More specifically, these membranes comprise phospholipids, phosphate-containing lipids comprising a hydrophobic end and a hydrophilic end that yield glycerol and fatty acids upon hydrolysis. More specifically, the most commonly occurring phospholipids in the human body are phosphoglycerides and sphingolipids. Phosphoglycerides, which are related to phosphatidic acid, comprise a phospholipid where one of the primary hydroxyl groups of glycerol is esterified to phosphoric acid that links to some base or polyol while the other hydroxyl groups are esterified to fatty acids. Sphingomyelin, the only sphingolipid that is a phospholipid, comprises three building-block components: one molecule of sphingosine or a related base as the backbone, one molecule of a fatty acid, and a polar head group.

The most abundant phospholipids are phosphatidylcholine (also known as lecithin), and phosphatidylethanolamine (also known as cephalin), phosphatidylserine, phosphatidylinositol, phosphatidylglycerol, and diphosphatidylglycerol are also found in human cells and tissues, but comprise a minority of the phosphoglycerides found. Phosphatidylcholine comprises more than about 75% of the phospholipids found in blood plasma and over about 20% of the phospholipids found in other tissues. Phosphatidylethanolamine, comprises more than 10% of phospholipids found in all tissues except blood plasma.

Plasmalogens, a subgroup of phospholipids, are basically phosphoglyceride analogs of the alkyl ether acylglycerols. They have a vinyl ether linkage to the fatty acid of the phospholipid, instead of to the normal ester. Plasmalogens are often found throughout the tissues of the human body, such as the brain, heart, lung, liver, kidney, testes, erythrocytes and blood plasma. The most abundant plasmalogen is ethanolamine plasmalogen (1-(1'-alkenyl)-2-acyl glycero-phosphatidylethanolamine), which is found in all tissues of the human body except for the heart, liver and blood plasma. A substantial amount of choline plasmalogen is found only in heart cells.

Phospholipids aid in the strengthening of tissues and cellular structures. They also possess some anti-oxidant properties, preventing cells from oxidizing and thereby aging. The amount of both phospholipids and plasmalogens available in the human physiology decreases, leading to the increased severity of age-related conditions.

Treatments that reduce the symptoms of aging are desirable. In particular, the ingestion of additional phospholipids, derived from outside mammalian sources, has been found to supplement the human body's internal supply of phospholipids. In the physiology of the human, phospholipids and plasmalogens have been found to aid in the treatment of age-related symptoms. Extracted mammalian phospholipids have had only limited success in treating age-related conditions.

BRIEF SUMMARY OF THE INVENTION

According to one aspect of the present invention, there is provided a composition for the prevention and treatment of age-related physical and mental disorders. This composition includes phospholipids that have been extracted from chick embryos aged between about 6 days old and about 14 days old.

According to another aspect of the present invention, there is provided a method for extracting phospholipids from chick embryos for use in a composition for alleviating age-related physical and mental disorders. The fertilized eggs are incubated for between about 6 days to about 14 days. The chick embryos are separated and the lipids of chick embryos are extracted by organic solvents. Phospholipids are separated from solvents and residual water by evaporation and freeze-drying.

According to yet another aspect of the present invention, there is provided a method for using a composition for preventing and treating age-related physical and mental disorders, in a human subject in need thereof. A dosage of a composition including phospholipids extracted from chick embryos incubated for between about 6 days and about 14 days is administered to the subject. The dosage is of a sufficient amount to increase physical endurance.

According to still another aspect of the present invention there is provided a method for treating age-related physical and mental disorders, in a human subject in need thereof. A dosage of the composition including phospholipids extracted from chick embryos incubated for between about 6 days and about 14 days is administered to the patient. The dosage is of a sufficient amount to increase physical endurance.

Other aspects of the present invention will become apparent in connection with the following description of the present invention.

DETAILED DESCRIPTION OF THE INVENTION

The present invention relates generally to the field of therapeutic uses of embryonic phospholipids, particularly plasmalogens of phosphoglycerides prepared from chicken embryo tissues, for prevention and treatment of age-related disorders. The present invention provides a composition for preventing and treating these age-related physical and cognitive disorders that comprises a phospholipid extract collected from 6 to 14 day-old chick embryos. The present invention comprises pharmaceutical compositions containing early chick embryo phospholipids, particularly those including plasmalogens, mixed into an inert, nontoxic carrier for oral or sublingual administration, and methods of preparing and administering these compositions.

There are generally two groups of phospholipids present in embryonic and post-natal chicken brains. The first group comprises phosphatidylcholine, phosphatidylethanolamine, phosphatidylserine and phosphatidylinositol. The second group comprises plasmalogens of choline, ethanolamine and serine. This second group also includes sphingomyelin, and ethanolamine ether phosphatides. In young chicken embryos, the phospholipids of the first group dominate the chemical makeup of the embryos. Up until chick embryos are about 16 days old, the phospholipids of the first group are synthesized very rapidly, while there is only a slight increase in the amount of phospholipids of the second group. When chick embryos are aged between about 16 and about 20 days old, the phospholipids of the second group begin to rapidly synthesize as well, bringing the level of phospholipids of the second group close to that of the first group. For the purposes of preventing and treating age-related illnesses, the preferred embryo age is between about 6 and about 14 days old; more preferably, the embryo age is between about 9 and about 10 days old.

Phospholipids in early to mid-stage embryos—those aged from about 6 to about 14 days—contain strikingly different phosphoglycerides than late-stage embryos. These mid-stage phosphogeycerides contain alkenyl and acyl groups not typically present in late stage phosphoglycerides. For example, mid-stage phosphoglycerides comprise ethanolamine plasmalogens with short chain lauric or myristic ester linkages and palmityl ether linkages.

Plasmalogens and phospholipids extracted from mid-stage embryos play an important role in the prevention and treatment of age-related disorders. For example, the presence of plasmalogens in substantial amounts in the inner layer of biological membranes is well-documented, indicating that these lipids are involved in signal transduction following binding regulatory mechanisms within these membranes. It is believed that there is specific participation by ether lipids in the chemiosmotic process, similar to the participation of such inner mitochondrial membrane components as coenzyme Q, NADH, FMN and cytochrome a $_3$. It is also believed that membrane lipid composition is strongly influenced by lipid shape, and that the observed changes in lipid composition serve to stabilize the bilayer arrangement of cellular and subcellular membranes. All these factors can strengthen the membranes of the cell's surface, as well as those of subcellular organelles, reducing the effects of age-related illnesses.

Plasmalogens also are potential protectors against the oxidation of LDL proteins. About 3% to about 5% of total LDL phospholipids are plasmalogens. In vitro oxidation of LDL using an oxidizing agent induces a selective reduction of plasmalogen subgroups in phosphatidylcholine and phosphatidylethanolamine. VLDL and LDL plasmalogens were oxidized to a greater extent (99% decrease) compared to HDL plasmalogens (35%), suggesting that plasmalogens play a protecting role with respect to atherogenesis, the build-up of fats and fatty acids in the blood stream. This also contributes to the regulation the blood pressure, which is also affected by age.

The content of cholesterol and phospholipids in 8 and 16 day old chick embryo fibroblasts has also been compared. Cholesterol content did not change, whereas total phospholipids decreased with time change, resulting in an increase of the cholesterol to phospholipid ratio. Further, the fatty acid composition of phosphatidylcholine and phosphatidylethanolamine in these fibroblasts showed unique features. For example, the content of myristic acid was depleted by more than two-thirds from the 8 to 16 day old fibroblast. This indicates a change in the fluidity of membranes during development, a change that aids in keeping cells relatively strong and helps to assuage age-related conditions.

To prepare a composition for preventing and treating age-related conditions, chick embryos are selected that are aged between about 6 days and about 14 days; preferably, between about 9 days and about 10 days. These embryos have been preferably incubated for the duration of aging at a temperature between about 90° F. to about 100° F., preferably between about 95° F. to about 100° F., more preferably between about 99° F. to about 100° F. The embryos are then stored until use by immediately freezing the embryos and storing them in a freezer at a temperature between about −70° C. to about −90° C., preferably between about −75° C. to about −85° C., more preferably between about −80° C. to about −85° C.

To prepare the frozen embryos for use, they are first thawed, and then briefly minced with a blender. The minced embryo pieces are then centrifuged by any method known to one of skill in the art. The centrifugation is performed in order to separate out the liquid portions of the embryos. Any residual water in the solid phase is then removed by further centrifugation methods after mixing with ethanol. The residual water may also be removed by freeze-drying methods, warm air currents, or any other dessication method known to one of skill in the art. If centrifugation methods are used with ethanol, acetone may be added to the ethanol to improve drying properties. In a large scale preparation, minced embryo tissues may be dried in an evaporator having a partial vacuum. In such an evaporator, the vacuum pressure should be maintained such that the boiling point of the minced tissues is between about 50° C. and about 60° C. Preferably, the vacuum pressure is maintained such that the boiling point is between about 54° C. and about 57° C. If necessary, a warm air current is used to further dry the condensed minced embryo mixtures. The air current should be maintained at about 180° C. to about 200° C., preferably at about 188° C. to about 192° C., for best results in drying the embryo pieces without chemically destroying the biological compounds.

The minced, dried embryo tissues are then mixed with suitable organic solvents, such as a hexane-ethanol solution, wherein the lipids in the minced embryo tissues are extracted into the organic solvent. Preferably, the lipids are extracted under stirring. As a result, a lipid extract is removed from the liquid phase, and the lipid extract is temporarily set aside. The liquid phase left after lipid extraction is then concentrated to about 5% to about 15% of the original volume, preferably concentrated to about 9% to about 11% of the original volume. This may be done by any method known in the art, but is preferably performed by using a flash evaporator at less than about 40° C. to about 50° C., more preferably at about 43° C. to about 46° C.

The liquid phase is then separated into an aqueous and organic layer. The organic layer is then further concentrated to create a phospholipid extract. In order to eliminate any residual water and organic solvents from the phospholipid extract, the extracted phospholipids can be lyophilized after mixing them with a portion of inactive ingredients. For example, an alimentary antioxidizing agent and isoleucine can be added to the lyophilized mixture. The phospholipid extract is preferably lyophilized by a standard freeze-drying method, but may be purified by any method known to those of skill in the art.

A small portion of the phospholipid extract is set aside and saved for quality analysis of the resulting lipids in the composition. Analysis can be performed by thin layer chromatography, high performance liquid chromatography (HPLC), gas chromatography, NMR spectrometry, or any combination of these techniques. Typically, NMR spectroscopy shows that as a result of this method, the phospholipid extract contains phosphatidylcholine comprising about 50% to about 70% of the total phospholipids, more preferably comprising about 55% to about 66% of the total phospholipids. Plasmalogens of phosphatidylcholine are generally not detected in any appreciable amount in the phospholipid extract resulting from this method. Phosphatidylethanolamine and its plasmalogen comprises about 20% to about 30% of the total phospholipids in the phospholipid extract, more preferably 23% to about 26% of the total phospholipids. Further analysis also shows that the major fatty acids found in the phospholipid extract include C18:0 and C16:0 (from phosphatidylethanolamine) and C16:0, C20:4n6, C16:1, C22:6n3, and C18:1 (from phosphatidylcholine). The chemical nomenclature used above indicates the length of the fatty acid (indicated by the number directly after the "C"), as well as the number of double bonds along its backbone (indicated by the number directly after the colon) and the position of these double bonds (indicated by the number after an "n").

To eliminate any residual water and organic solvent, the phospholipid extracts are lyophilized after mixing them with an alimentary antioxidizing agent and amino acids. Amino acids are a basic building block of the human body, and supplements including these amino acids serve to help replenish those levels. Any amino acid that is hydrophobic may be used in this compound. Common amino acids, such as lysine, leucine, isoleucine and cyteine may be used. More preferably, isoleucine is used. A particularly hydrophobic amino acid, isoleucine is often found concentrated in muscle tissues. In particular, isoleucine aids the formation of hemoglobin in the human body. Isoleucine also serves to stabilize and regulate blood sugar and energy levels throughout the body.

Further, the phospholipid extract can be lyophilized or otherwise admixed with an antioxidant. Antioxidant compounds are those that reduce the oxidization of the cellular structure. This slows the cellular aging process, and keeps cells stronger. In the present mixture, the addition of antioxidants serves to help prevent the oxidation of phospholipids. Preferred antioxidants for use in the composition comprise vitamin E, as well as its derivatives, and vitamin C, as well as its derivatives. More preferably, vitamin E and ascorbyl palmitate, a vitamin C derivative, are used. Vitamin E, a fat-soluble, naturally occurring vitamin, has particularly good anti-oxidant properties. Vitamin E has been linked to a reduction in the rate of coronary diseases. Vitamin C serves not only to prevent cellular oxidation, but also to aid the synthesis of collagen in the body, which itself helps to repair aged skin and muscle tissues. Ascorbyl palmitate has been shown to be a particularly effective derivative of vitamin C in supplements. These antioxidants may also replace the amino acids in an embodiment of the present invention.

Additionally, a binding element is preferably added to the phospholipid extract. The binding element serves to hold the ingredients of the composition together. Any stearate-based compound safe for human consumption may be used, such as calcium stearate and zinc stearate. However, a preferred binding element is magnesium stearate. A derivative of magnesium, this chemical compound is often used as a food additive to promote binding in food products.

Polysaccharides, which are carbohydrate-based starches comprising a plurality of sugar molecules, also help to hold the ingredients of the composition together. Any polysaccharide may be used; however, preferred polysaccharides in the composition include lactose, cellulose, and fructose. More preferably, lactose and cellulose are used.

Other ingredients may also be added to improve the taste or consistency of the final formulation, as is known in the art. For example, a flavoring agent may be added to the composition. Such a flavoring agent would improve the taste of the composition upon administration, letting it taste more like mint, fruit, or any taste preferred by the consumer. Use of a flavoring agent is preferable in a composition to be administered in a liquid form, but may also be used in a solid form composition.

After preparing the phospholipid extract, the chosen ingredients are then mixed together to create doses of the final composition. This composition may be in a liquid form or a solid capsule form. The composition may be administered in any form known to those in the art; for example, a solid capsule may be a film-coated tablet or a soft gelatin tablet. As a further example, a liquid composition may be administered as a liquid elixir or as a sublingual or oral spray. While the form of administration may change, the dosage should be calculated such that a single dosage comprises about 40 mg to about 100 mg of phospholipid extract. More preferably, a single dosage comprises about 50 mg to about 80 mg of phospholipid extract.

The examples below show different embodiments of the composition, showing alternate ingredients for the composition to make them more suited for different final forms and administration methods for the final composition.

EXAMPLE I

Sublingual Film-Coated Tablets from Chick Embryo Phospolipids

| Chick Embryo Phospholipids | 50–80 g |
|---|---|
| Isoleucine | 30 g |
| Vitamin E | 25 g |
| Ascorbyl palmitate | 10 g |
| Magnesium stearate | 15 g |
| Cellulose | 10 g |
| Lactose | 10 g |

In this Example, the chick embryo phospholipids are processed as above. The processed phospholipid extract is then combined with the other ingredients and mixed together. As is known in the art, caplets are then created by pouring the mixture into a caplet mold, and allowing the mixture to set. The caplets are released from the mold via a releasing agent, such as a wax, grease, or film. The particular quantities of each component above produce enough of the composition to create approximately 1,000 film-coated tablets.

EXAMPLE II

Sublingual Liquid Suspensions of Chick Embryo Phospholipids

| Embryo phospholipids | 12.5–20 g |
|---|---|
| Vitamin E | 2 g |

-continued

| | |
|---|---|
| Vitamin C | 2 g |
| Fructose | 2 g |
| Peppermint flavoring oil | 3 g |
| Emulsifier (i.e., Tween 80) | 1.5 g |
| Carrier ethyl alcohol | to fill |
| Purified water | to fill |

Phospholipid extract prepared by the above methods can be used in this example. The first six ingredients listed above are combined and mixed together, and the carrier ethyl alcohol and purified water are then added in equal amounts to create a total of 1000 ml of solution. A peppermint flavoring oil is a preferred flavoring elixir; however, it may be substituted with another flavor, or eliminated. As is known in the art, the ingredients are thoroughly mixed together to create a liquid composition, and dispensed in doses of about 2 ml to about 10 ml; preferably, in doses of about 3 ml to about 6 ml.

Note that an amino acid is not used in the present Example. However, the relative amounts of antioxidants to phospholipids are adjusted so as to maintain the proper balance between the two ingredients.

EXAMPLE III

Intraoral Spray Aerosols of Chick Embryo Phospholipids

Percentage by Weight

| | |
|---|---|
| Embryo phospholipids | 1.25–2.0 |
| Vitamin E | 1.5 |
| Vitamin C | 1.5 |
| Peppermint flavoring oil | 3.0 |
| Fructose | 2.0 |
| Emulsifier | 0.1 |
| Carrier ethyl alcohol | 89.9–90.65 |

The above example is directed towards an intraoral spray dosage mechanism, a spray that is directed into the mouth. As in Example II, the amino acid is also omitted in this Example. Here, the removal of the amino acid maintains a sprayable liquid consistency for the mixed composition. Further, as in Example II, the peppermint flavoring oil may be substituted with another flavor, or omitted. The resulting composition is then poured into a spray container able to dispense measured dosages, as is known in the art. Each measured dosage is about 2 ml to about 10 ml of solution; preferably, each dose is about 3 ml to about 6 ml of solution.

EXAMPLE IV

Oral Soft-Gel Tablets of Chick Embryo Phospholipids

| | |
|---|---|
| Embryo phospholipids | 50–80 g |
| Vitamin E | 25 g |
| Ascorbyl palmitate | 10 g |
| Vegetable oil | 30 g |
| Glycerol | 20 g |
| Gelatin | to fill |

In this example, an alternate formulation, including alternate binding elements more appropriate for a soft gel dosage, is presented for the composition of Example I. The method of making a soft gel tablet is well known in the art, and is similar to that of Example I. These ingredients will produce enough composition for about 1000 soft-gel tablets.

EXAMPLE V

Oral Film-Coated Tablets of Chick Embryo Phospholipids

| | |
|---|---|
| Embryo phospholipids | 50–80 g |
| Isoleucine | 80 g |
| Vitamin E | 30 g |
| Ascorbyl palmitate | 10 g |
| Magnesium stearate | 15 g |
| Calcium gluconate | 20 g |
| Sorbitol | 40 g |
| Ethyl cellulose | 15 g |

In this example, an alternate formulation, including alternate binding elements, is presented for the film-coated tablets of Example I. As in Example I, these ingredients will produce enough composition for about 1000 film-coated tablets.

The above examples are presented as representative suggested methods of dosage. The preferred dosage level is between about one dose and about three doses per day, more preferably a single dose per day Phospholipid extract from chick embryos aged between about 6 days to about 14 days, processed as shown in Example I above, were tested in 15 month-old male mice for the effect of the embryo phospholipids on longevity. It is well-known in the art that the effects of this composition on a 15 month-old male mouse is comparable to the effect of the composition on humans of approximately 40 to 45 years of age. A total of 100 NIA balb/cNNia mice were divided into 3 groups. The first group of 30 mice was given only a saline solution. The second group of 30 mice was given a composition processed as by Example I above, but using the portion of the chick embryo extract without phospholipids in place of the phospholipid extract. The final group of 40 mice was given a composition processed as by Example I above using the chick embryo phospholipid extract. Each group was given an oral dosage once a week. During the first 10 months of the experiment, only one of the 40 mice (2.5%) treated with chick embryo phospholipids died, while 7 out of 30 mice (23.3%) in the group given saline solution and 7 out of 30 mice (23.3%) in the group given non-phospholipid chick embryo extract composition died.

For the full extent of the experiment, the survival pattern of the group given non-phospholipids was essentially similar to that of the control group. In contrast, the group given the composition containing phospholipid extract had a significantly lower mortality rate, as shown in Table I.

TABLE I

Mortality Rate of Mice

| Mortality Rate | Time to Achieve Mortality Rate (Control Groups) | Time to Achieve Mortality Rate (Phospholipid Groups) |
|---|---|---|
| 10% | 3.0 months | 11.8 months |
| 20% | 8.4 months | 13.2 months |
| 30% | 10.8 months | 14.2 months |

TABLE I-continued

Mortality Rate of Mice

| Mortality Rate | Time to Achieve Mortality Rate (Control Groups) | Time to Achieve Mortality Rate (Phospholipid Groups) |
|---|---|---|
| 40% | 13.2 months | 15.3 months |
| 50% | 14.2 months | 16.0 months |

Tests were also run on 21 human subjects aged between about 47 years old and about 70 years old. A composition containing the phospholipid extract, prepared as in Example I, was given in an oral dosage twice per week for 8 weeks. Each administered dose was equivalent to the phospholipids contained in ten chick embryos aged about 10 days each, which is between about 40 mg and about 100 mg of phospholipid extract.

The efficacy of the phospholipid extract derived from the chick embryos aged between about 6 days and about 14 days on the human subjects was tested subjectively, based on statements made by the patients at 4 weeks, 8 weeks, and weeks after the initiation of the experiment. The questionnaire on which the statements were based included the evaluation of work performance, emotional stability, mental and physical tiredness, headache, sleep pattern, appetites, digestion of food, sexual performance, hair and nail growth, and other noticeable changes in physical and mental activity. Significant positive responses to a majority of these inquiries were found in more than 60% of subjects. Further, considerable improvement in physical endurance tests was also observed. An additional biochemical study on the subjects showed noticeable improvement in blood platelet count, liver enzyme values (such as alkaline phosphatase and lactic dehydrogenase), total cholesterol level, and fasting glucose value.

Although the invention herein has been described in connection with a preferred embodiment thereof, it will be appreciated by those skilled in the art that additions, modifications, substitutions, and deletions not specifically described may be made without departing from the spirit and scope of the invention as defined in the appended claims.

The invention claimed is:

1. A composition for alleviating age-related physical and mental disorders, comprising phospholipids extracted from chick embryos aged between about 6 days old and about 14 days old, wherein said phospholipids comprise about 50% to about 70% by weight of phosphatidylcholine and about 20% to about 30% by weight of phosphatidylethanolamine and its plasmalogens.

2. The composition of claim 1 wherein said chick embryos are aged between about 9 days old and about 10 days old.

3. The composition of claim 1 further comprising at least one amino acid.

4. The composition of claim 3 wherein said amino acid is chosen from the group consisting of isoleucine, lysine, leucine, and cysteine.

5. The composition of claim 4 wherein said amino acid comprises isoleucine.

6. The composition of claim 1 further comprising at least one antioxidant.

7. The composition of claim 6 wherein said at least one antioxidant is chosen from the group consisting of vitamin E, vitamin E derivatives, vitamin C, and vitamin C derivatives.

8. The composition of claim 6 wherein said at least one antioxidant comprises vitamin E and ascorbyl palmitate.

9. The composition of claim 1 further comprising at least one binding element.

10. The composition of claim 9 wherein said at least one binding element is a stearate compound.

11. The composition of claim 10, wherein said at least one binding element is selected from the group consisting of magnesium stearate, calcium stearate, and zinc stearate.

12. The composition of claim 11, wherein said at least one binding element comprises magnesium stearate.

13. The composition of claim 1 further comprising at least one polysaccharide.

14. The composition of claim 13 wherein said at least one polysaccharide is chosen from the group consisting of fructose, lactose and cellulose.

15. The composition of claim 14 wherein said at least one polysaccharide comprises lactose and cellulose.

16. The composition of claim 1 further comprising a flavoring agent.

17. A composition for alleviating age-related physical and mental disorders, comprising: phospholipids extracted from chick embryos aged between about 6 days old and about 14 days old and comprising about 50% to about 70% by weight of phosphatidylcholine and about 20% to about 30% by weight of phosphatidylethanolamine and its plasmalogens; isoleucine; vitamin E; ascorbyl palmitate; magnesium stearate; lactose; and cellulose.

18. The composition of claim 17, wherein said chick embryos are aged between about 9 days old and about 10 days old.

19. A method for extracting phospholipids from chick embryos for use in a composition for alleviating age-related physical and mental disorders, comprising: incubating said chick embryos for between about 6 days to about 14 days; preparing said chick embryos for chemical extraction; extracting lipids from said chick embryos comprising about 50% to about 70% by weight of phosphatidylcholine and about 20% to about 30% by weight of phosphatidylethanolamine and its plasmalogens; separating phospholipids out of said lipids; and lyophilizing said phospholipids.

20. The method of claim 19, wherein said chick embryos are incubated for between about 9 days to about 10 days.

21. A method of alleviating a physical or mental disorder selected from the group consisting of improving work performance, improving emotional stability, decreasing mental tiredness, decreasing physical tiredness, decreasing the incidence of headaches, improving sleep, improving appetite, improving the digestion of food, improving sexual performance, improving hair and nail growth, and improving physical endurance comprising:
    extracting phospholipids from chick embryos incubated for between about 6 days and about 14 days comprising about 50% to about 70% by weight of phosphatidylcholine and about 20% to about 30% by weight of phosphatidylethanolamine and its plasmalogen; and
    administering to a human subject in need thereof a dosage of a composition comprising said phospholipids, wherein said dosage is of a sufficient amount to treat the disorder.

22. The method of claim 21, wherein said chick embryos are incubated for between about 9 days and about 10 days.

23. The method of claim 21, wherein the form of said composition is selected from the group consisting of: tablet form, liquid elixir form, and intraoral spray form.

24. The method of claim 21, wherein said composition comprises between about 40 mg and about 100 mg of phospholipids.

25. The method of claim 24, wherein said composition comprises between about 50 mg and about 80 mg of phospholipids.

26. A method for alleviating age-related conditions selected from the group consisting of improving work performance, improving emotional stability, decreasing mental tiredness, decreasing physical tiredness, decreasing the incidence of headaches, improving sleep, improving appetite, improving the digestion of food, improving sexual performance, improving hair and nail growth, and improving physical endurance, comprising
ingesting a dosage of a composition comprising phospholipids extracted from chick embryos incubated for between about 6 days and about 14 days comprising about 50% to about 70% by weight of phosphatidylcholine and about 20% to about 30% by weight of phosphatidylethanolamine and its plasmalogens; wherein said dosage is sufficient to treat the condition.

27. The method of claim 26, wherein said chick embryos are incubated for between about 9 days and about 10 days.

28. The method of claim 26, wherein said dosage is ingested orally.

29. The method of claim 28, wherein the form of said dosage is selected from the group consisting of: tablet form, liquid elixir form, and intraoral spray form.

30. The method of claim 28, wherein said dosage comprises between about 40 mg and about 100 mg of phospholipids.

31. The method of claim 30, wherein said dosage comprises between about 50 mg and about 80 mg of phospholipids.

* * * * *